(12) United States Patent
Ben-Eliezer et al.

(10) Patent No.: US 11,841,410 B2
(45) Date of Patent: Dec. 12, 2023

(54) METHOD AND SYSTEM FOR ANALYZING MULTI-COMPONENT MAGNETIC RESONANCE SIGNALS

(71) Applicants: Ramot at Tel-Aviv University Ltd., Tel-Aviv (IL); Yeda Research and Development Co. Ltd., Rehovot (IL)

(72) Inventors: Noam Ben-Eliezer, Tel-Aviv (IL); Noam Omer, Tel-Aviv (IL); Meirav Galun, Rehovot (IL)

(73) Assignees: Ramot at Tel-Aviv University Ltd., Tel-Aviv (IL); Yeda Research and Development Co. Ltd., Rehvot (IL)

( * ) Notice: Subject to any disclaimer, the term of this patent is extended or adjusted under 35 U.S.C. 154(b) by 0 days.

(21) Appl. No.: 17/585,812

(22) Filed: Jan. 27, 2022

(65) Prior Publication Data
US 2022/0236356 A1     Jul. 28, 2022

Related U.S. Application Data

(60) Provisional application No. 63/142,019, filed on Jan. 27, 2021.

(51) Int. Cl.
*G01R 33/50* (2006.01)
*G01R 33/56* (2006.01)
*A61B 5/055* (2006.01)

(52) U.S. Cl.
CPC .............. *G01R 33/50* (2013.01); *A61B 5/055* (2013.01); *G01R 33/5602* (2013.01); *G01R 33/5608* (2013.01)

(58) Field of Classification Search
CPC ........................ G01R 33/50; G01R 33/5602; G01R 33/5608; A61B 5/055
See application file for complete search history.

(56) References Cited

U.S. PATENT DOCUMENTS

2015/0355298 A1* 12/2015 Ben-Eliezer ........... A61B 5/055
                                                                              324/309
2019/0365273 A1* 12/2019 Jara ....................... A61B 5/0042
(Continued)

OTHER PUBLICATIONS

Alonso-Ortiz et al. "MRI-Based Myelin Water Imaging: A Technical Review", Magnetic Resonance in Medicine, 73(1): 70-81, Mar. 6, 2014.
(Continued)

*Primary Examiner* — Gregory H Curran

(57) ABSTRACT

Method for mapping the transverse relaxation times ($T_2$) in a magnetic resonance imaging (MRI) scan defined over a plurality of pixels, where each pixel is associated with a multicomponent $T_2$ ($mcT_2$) signal, comprises: accessing a computer readable medium storing an $mcT_2$ dictionary having a set of synthetic $mcT_2$ signals, and selecting a subset of synthetic $mcT_2$ signals for which correlations between the synthetic $mcT_2$ signals and pixels in the MRI scan are highest among the set. For each of at least a portion of the pixels, a respective $mcT_2$ scan signal is fitted to the subset to provide, a plurality of $T_2$ values for the pixel. A $T_2$ map of the MRI scan is generated based on the $T_2$ values.

20 Claims, 12 Drawing Sheets
(8 of 12 Drawing Sheet(s) Filed in Color)

(56) References Cited

U.S. PATENT DOCUMENTS

2020/0225304 A1* 7/2020 Kartaeusch ........ G01R 33/4828
2022/0252688 A1* 8/2022 Doneva ............. G01R 33/5615

OTHER PUBLICATIONS

Ben-Eliezer et al. "Rapid and Accurate T2 Mapping From Multi-Spin-Echo Data Using Bloch-Simulation-Based Reconstruction", Magnetic Resonance in Medicine, 73(2): 809-817, Published Online Mar. 19, 2014.

Bouhrara et al. "Improved Determination of the Myelin Water Fraction in Human Brain Using Magnetic Resonance Imaging Through Bayesian Analysis of McDESPOT", NeuroImage, 127: 456-471, Published Online Oct. 22, 2015.

Heath et al. "Advances in Noninvasive Myelin Imaging", Developmental Neurobiology, 78(2): 136-151, Published Online Nov. 10, 2017.

Hennig "Multiecho Imaging Sequences With Low Refocusing Flip Angles", Journal of Magnetic Resonance, 78(3): 397-407, Jul. 1988.

Laule et al. "Water Content and Myelin Water Fraction in Multiple Sclerosis. A T2 Relaxation Study", Journal of Neurology, 251(3): 284-293, Mar. 2004.

MacKay et al. "Magnetic Resonance of Myelin Water: An In Vivo Marker for Myelin", Brain Plasticity, 2(1): 71-91, Dec. 21, 2016.

McCreary et al. "Multiexponential T2 and Magnetization Transfer MRI of Demyelination and Remyelination in Murine Spinal Cord", NeuroImage, 45(4): 1173-1182, Published Online Jan. 21, 2009.

Moeller et al. "Iron, Myelin, and the Brain: Neuroimaging Meets Neurobiology", Trends in Neurosciences, 42(6): 384-401, Published Online Apr. 29, 2019.

West et al. "Myelin Volume Fraction Imaging With MRI", NeuroImage, 182: 511-521, Published Online Dec. 23, 2016.

Whittall et al. "In Vivo Measurement of T2 Distributions and Water Contents in Normal Human Brain", Magnetic Resonance in Medicine, MRM, 37(1): 34-43, Jan. 1997.

Whittall et al. "Quantitative Interpretation of NMR Relaxation Data", Journal of Magnetic Resonance, 84(1): 134-152, Aug. 1989.

Zhang et al. "Comparison of Myelin Water Fraction Brain Images Using Multi-Echo T2-Weighted GRASE Relaxation and Steady-State Methods", Proceedings of the International Society for Magnetic Resonance in Medicine, ISMRM 21st Annual Meeting & Exhibition, Salt Lake City, Utah, USA, Apr. 20-26, 2013, Poster, # 1103, Apr. 20, 2013.

* cited by examiner

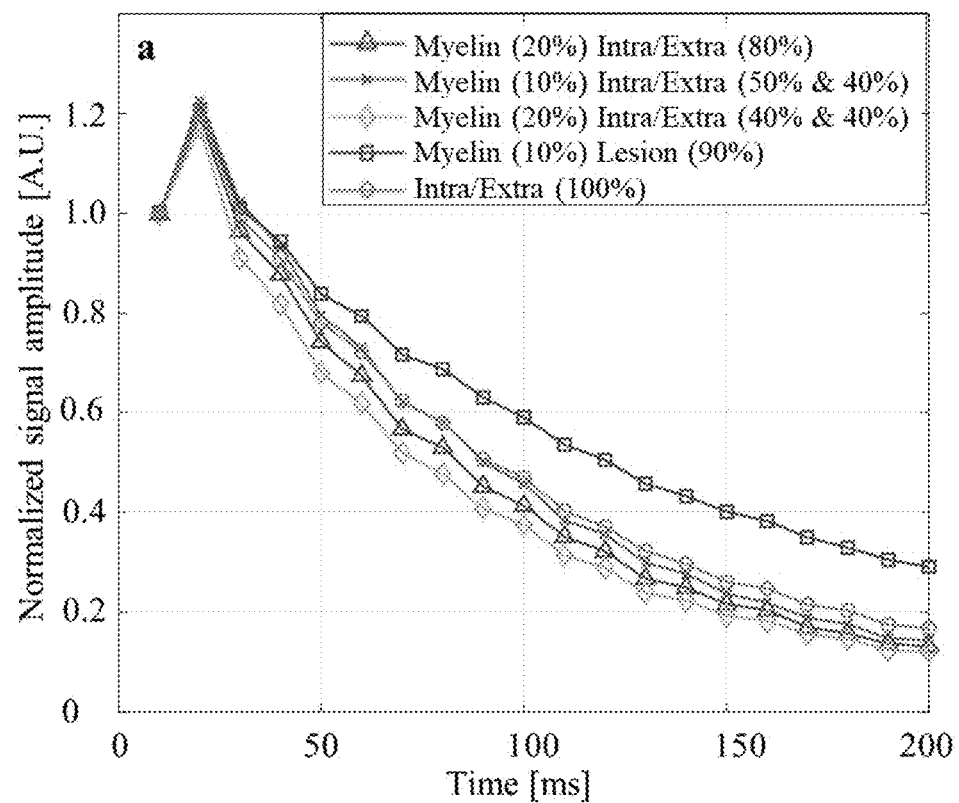
FIG. 1A
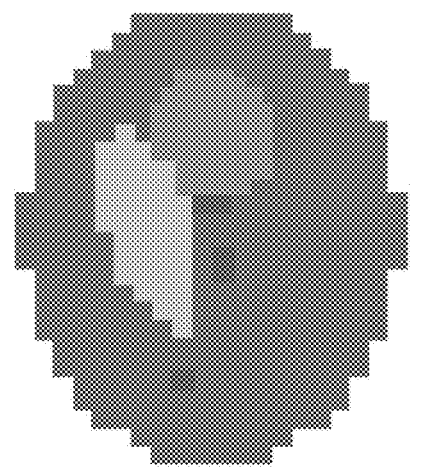
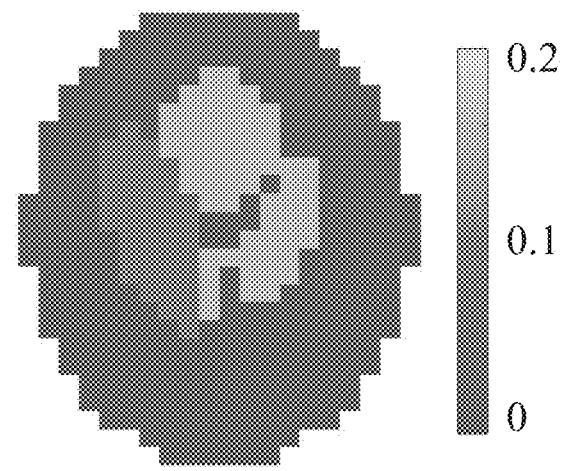
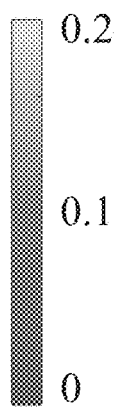
FIG. 1B　　　　　　　　FIG. 1C

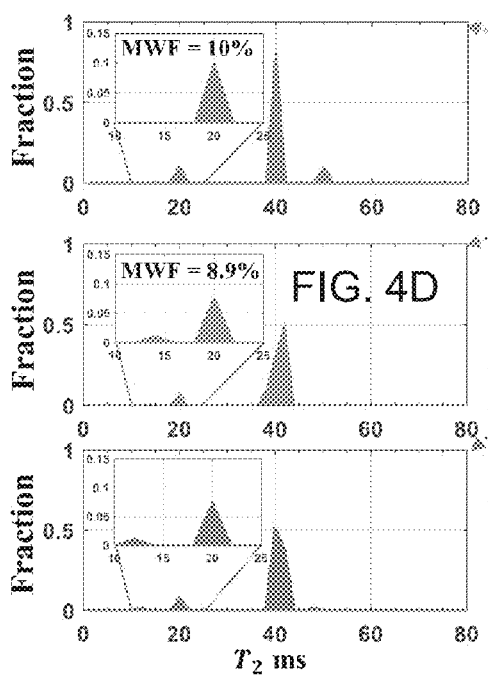
FIG. 4C
FIG. 4D
FIG. 4B
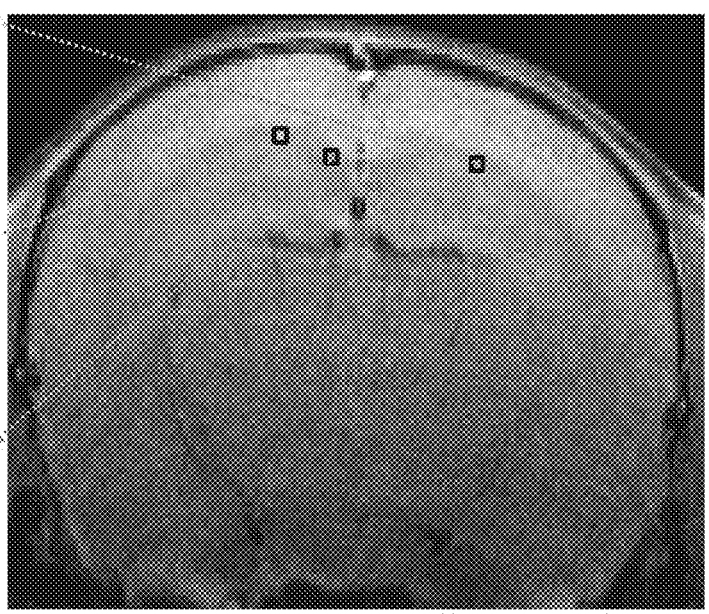
$T_2$-weighted image of mouse brain
FIG. 4A

| Selected ROI | Scan 1 | Scan 2 | Scan 3 |
GCC
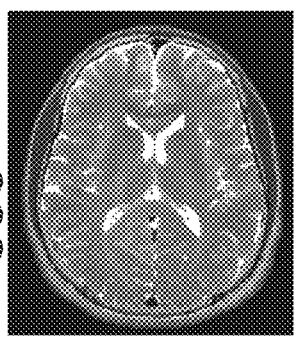 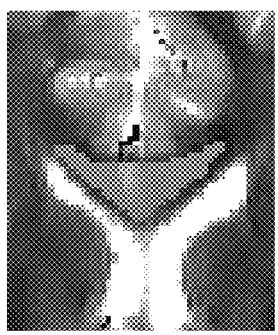 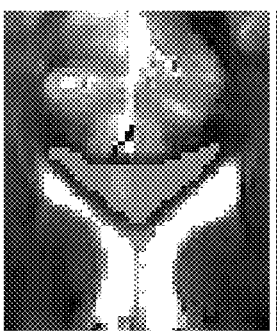 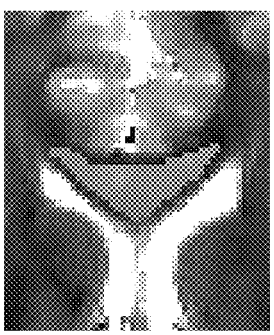
FIG. 9A    FIG. 9B    FIG. 9C    FIG. 9D
SCC
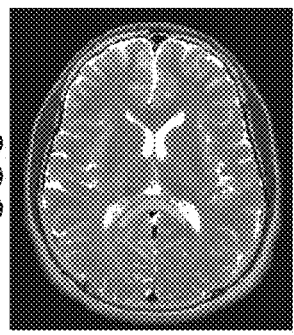 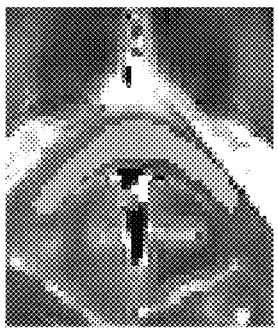 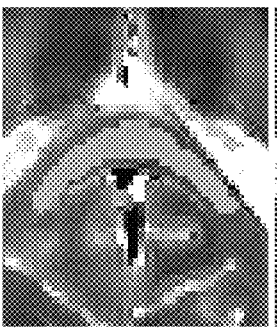 
FIG. 9E    FIG. 9F    FIG. 9G    FIG. 9H
Cortical WM
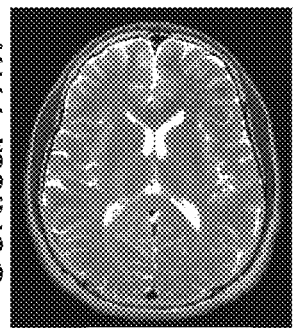   
FIG. 9I    FIG. 9J    FIG. 9K    FIG. 9L
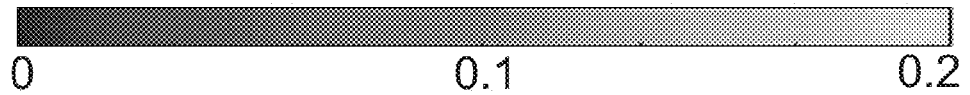
0           0.1          0.2

METHOD AND SYSTEM FOR ANALYZING MULTI-COMPONENT MAGNETIC RESONANCE SIGNALS

RELATED APPLICATION(S)

This application claims the benefit of priority under 35 USC § 119(e) of U.S. Provisional Patent Application No. 63/142,019 filed on Jan. 27, 2021, the contents of which are incorporated by reference as if fully set forth herein in their entirety.

FIELD AND BACKGROUND OF THE INVENTION

The present invention, in some embodiments thereof, relates to a magnetic resonance and, more particularly, but not exclusively, to a method and system for analyzing multi-component magnetic resonance signals.

Magnetic Resonance Imaging (MRI) is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

A nucleus can experience NMR only if it has a nonzero nuclear spin 'I', i.e., the nucleus has at least one unpaired nucleus. Examples of non-zero spin nuclei frequently used in MRI include $^1$H (I=1/2), $^2$H (I=1), $^{23}$Na (I=3/2), etc. When placed in a magnetic field, a nucleus having a spin I is allowed to be in a discrete set of energy levels, the number of which is determined by I, and the separation of which is determined by the gyromagnetic ratio of the nucleus and by the magnetic field. Under the influence of a small perturbation, manifested as a radiofrequency magnetic field, which rotates about the direction of a primary static magnetic field, the nucleus has a time dependent probability to experience a transition from one energy level to another. With a specific frequency of the rotating magnetic field, the transition probability may reach the value of unity. Hence at certain times, a transition is forced on the nucleus, even though the rotating magnetic field may be of small magnitude relative to the primary magnetic field. For an ensemble of spin I nuclei the transitions are realized through a change in the overall magnetization.

Once a change in the magnetization occurs, a system of spins tends to restore its magnetization to a longitudinal equilibrium value, by the thermodynamic principle of minimal energy. The time constant which control the elapsed time for the system to return to the equilibrium value is called "spin-lattice relaxation time" or "longitudinal relaxation time" and is denoted as $T_1$. An additional time constant, $T_2$ (≤T1), called "spin-spin relaxation time" or "transverse relaxation time", controls the elapsed time in which the transverse magnetization diminishes, by the principle of maximal entropy.

Over the past decades, attempts have been made to improve sensitivity of magnetic resonance (MR) techniques, particularly when studying pathologies in brain white matter (WM) that may appear to be normal without such an improvement. Specifically, since the water signal in human brain can be separated into three components each having a different characteristic $T_2$ value, these attempts are based on a multicomponent $T_2$ (mcT$_2$) analysis in which the $T_2$ relaxation decay curve is decomposed into exponential components [7].

SUMMARY OF THE INVENTION

Currently, mcT$_2$ is done through a fitting process where a weighted sum of different $T_2$ components (also referred to in the literature as $T_2$ spectra) is matched to multi-echo spin-echo (MESE) signal decay curve.

According to some embodiments of the present invention, it provides a method for mapping the transverse relaxation times ($T_2$) in an MRI scan. The MRI scan is defined over a plurality of pixels, each being associated with a multicomponent $T_2$ (mcT$_2$) signal. The method comprises of accessing a computer readable medium storing an mcT$_2$ dictionary having a set of synthetic mcT$_2$ signals, and selecting a subset of synthetic mcT$_2$ signals for which correlations between the synthetic mcT$_2$ signals and pixels in the MRI scan are highest among the set. For each of at least a portion of the pixels, a respective mcT$_2$ scan signal is fitted to the subset to provide, a plurality of $T_2$ values for the pixel. A displayed $T_2$ map of the MRI scan is generated based on the $T_2$ values.

According to some embodiments of the invention the method is executed without any a priori selection of a number of different $T_2$ values for the pixel.

According to some embodiments of the invention the correlations are obtained by calculating L2-norms or other similarity correlation test.

According to some embodiments of the invention the method comprises summing correlations across multiple pixels for each synthetic mcT$_2$ signal, wherein the selection is based on the summations.

According to some embodiments of the invention the method comprises constructing the mcT$_2$ dictionary.

According to some embodiments of the invention the method comprises receiving MR scan protocol parameters associated with the mcT$_2$ scan signals, wherein the constructing the is based on the scan protocol parameters.

According to some embodiments of the invention the method comprises constructing a single-component $T_2$ (scT$_2$) dictionary having a set of synthetic scT$_2$ signals, wherein the mcT$_2$ dictionary is constructed by calculating each synthetic mcT$_2$ signal as a combination of a plurality of synthetic scT$_2$ signals.

According to some embodiments of the invention the scT$_2$ is constructed by selecting a plurality of different predetermined $T_2$ values, and generating each synthetic scT$_2$ signal as a simulated echo modulation curve for one of the predetermined $T_2$ values.

According to some embodiments of the invention the method comprises prior to the selection, identifying a range of $T_2$ values for the at least the portion of the pixels, and diluting the mcT$_2$ dictionary based on the identified range.

According to some embodiments of the invention the method comprises denoising the MRI scan, prior to the selection.

According to some embodiments of the invention the MRI scan is a multiple echo spin-echo MRI scan.

According to some embodiments of the invention the MRI scan is a preclinical MRI scan.

According to some embodiments of the invention the MRI scan is a clinical MRI scan.

According to some embodiments of the invention the MRI scan comprises an MRI scan of a brain.

According to some embodiments of the invention the MRI scan comprises an MRI scan of a skeletal muscle.

According to some embodiments of the invention the MRI scan comprises an MRI scan of a cartilage.

According to some embodiments of the invention the MRI scan comprises an MRI scan of a breast.

According to some embodiments of the invention at least one of the $T_2$ values corresponds to a water fraction selected from the group consisting of intracellular water fraction, and extracellular water fraction.

According to some embodiments of the invention at least one of the $T_2$ values corresponds to a myelin water fraction (MWF).

According to some embodiments of the invention at least one of the $T_2$ values corresponds to a macromolecule-bound water fraction.

According to some embodiments of the invention at least one of the $T_2$ values corresponds to a solid macromolecule.

According to an aspect of some embodiments of the present invention there is provided a computer software product, comprising a computer-readable medium in which program instructions are stored, which instructions, when read by a data processor, cause the data processor to receive at least an MRI scan, and to execute the method as delineated above and optionally and preferably as further detailed below.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A and 1B show numeric phantom design. Simulated signals were produced based on clinical Multi-echo-spin-echo (MESE) protocol parameters and arranged in a 2D segment to resemble myelinated brain tissue. FIG. 1A shows five ensembles of simulated $T_2$-signals weighted by different $T_2$ fractions associated, for example, with myelinated brain tissue composition. Exact fractions are listed within the figure. FIG. 1B is a 2D display of the Shepp-Logan shape phantom presenting the distribution of the 5 multi-$T_2$ signals within the segment with different colors.

FIG. 1C is a 2D display of a matching myelinated brain tissue composition (corresponding to the Myelin fractions in the legend of FIG. 1A). Prior to the reconstruction, white Gaussian noise of varying SNRs (200,150,100 and 60) to the simulated signals, Additionally, the physiological variability in $T_2$ values within a tissue was modeled by simulating random variations of ±15% in the $T_2$ values of each tissue component.

FIGS. 2A-E show reconstruction of simulated MESE data. Fitted $T_2$ distributions (dotted orange line) vs. the actual ones (continuous blue line) from noisy simulated MESE signals (SNR 60 and variability ±20% from the true $T_2$ values within segment). $T_2$ distributions are marked with matching segment colors.

FIGS. 3A-D show validation of an mcT$_2$ fitting algorithm, performed according to some embodiments of the present invention.

FIG. 4A shows a $T_2$-weighted image of a mouse brain (coronal slice) acquired using MESE protocol with 9.4 Tesla Bruker scanner (2nd echo, echo-time=8.5 ms).

FIGS. 4B-D show examples of three reconstructed $T_2$ spectra from different locations along the corpus-callosum. The pixels and their corresponding spectra are indicated with matching colors.

Figure 5A:
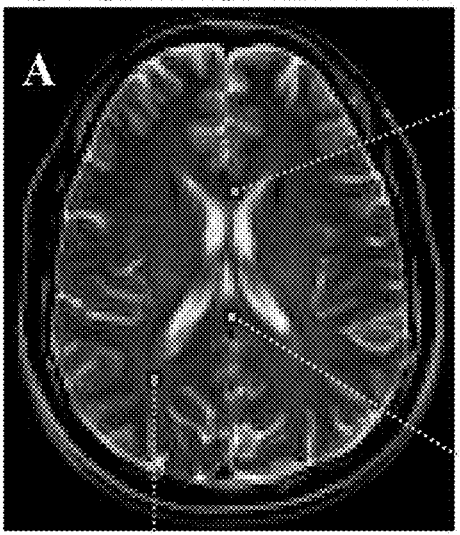

FIG. 5A shows a $T_2$-weighted image of human brain (axial slice).

Figure 5B:
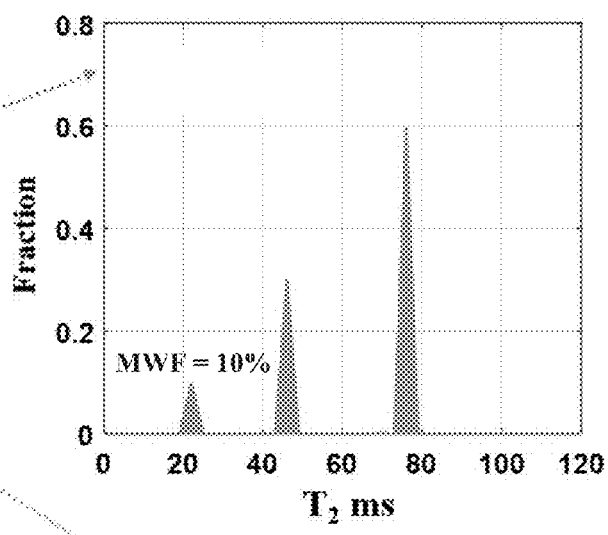
Figure 5C:
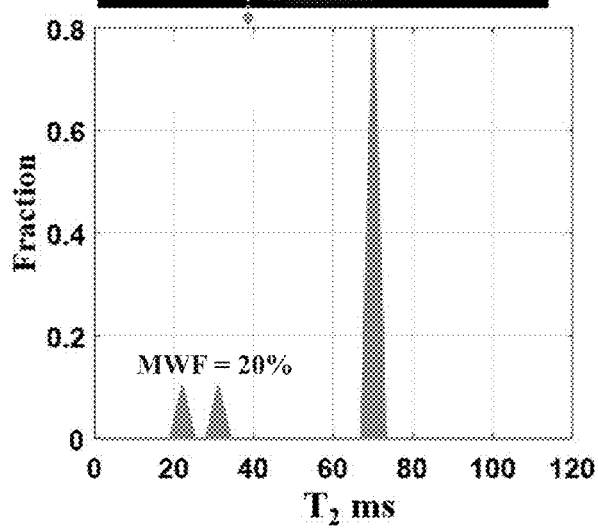
Figure 5D:
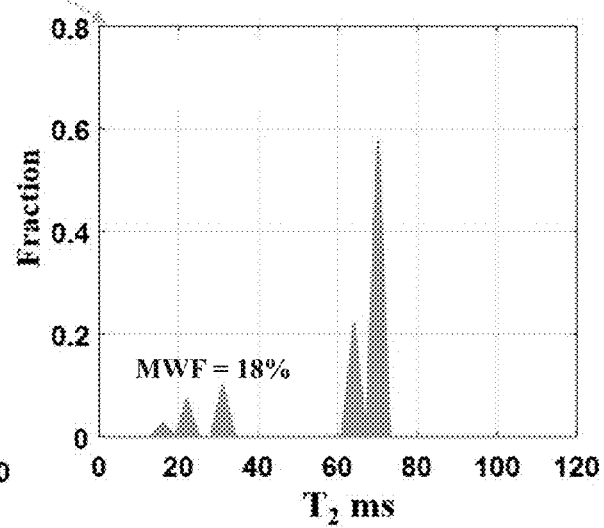

FIGS. 5B-D show examples of three reconstructed $T_2$ spectra from different WM human segments, where FIG. 5B shows the splenium of corpus-callosum (blue), FIG. 5C shows posterior thalamic radiation (green), and FIG. 5D shows genu of corpus-callosum (orange). Different $T_2$ compartments associated with intra and extra cellular matrix are indicated in black arrows. Estimated MWF ($T_2$<40 ms) are indicated with black boxes at the right corners.

Figure 6:
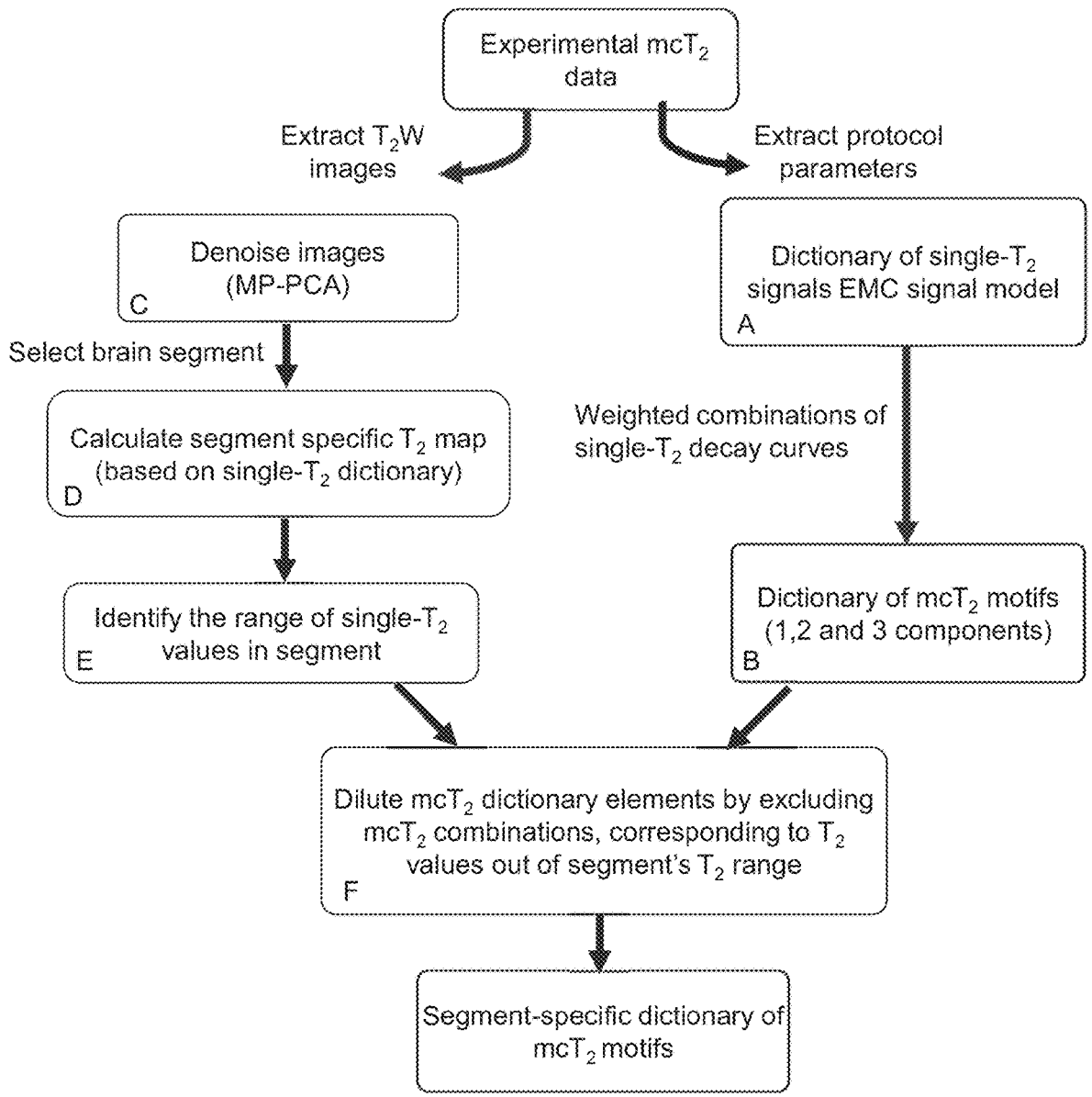
Figure 7:
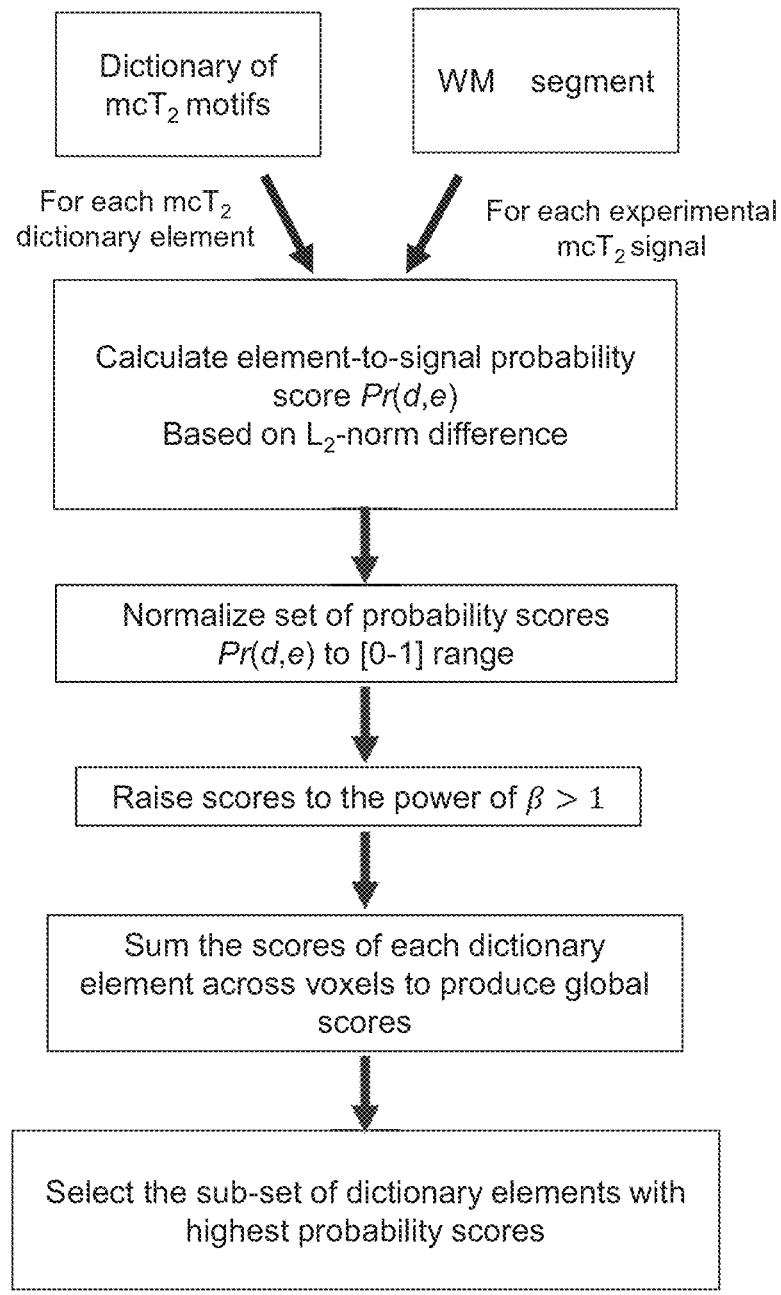

FIG. 6 is a flowchart showing a method suitable for constructing a data driven mc-$T_2$ signals dictionary, according to some embodiments of the present invention;

FIG. 7 is a flowchart showing a method suitable for selecting a segment-specific set of mcT$_2$ basis elements, according to some embodiments of the present invention.

Figure 8A:
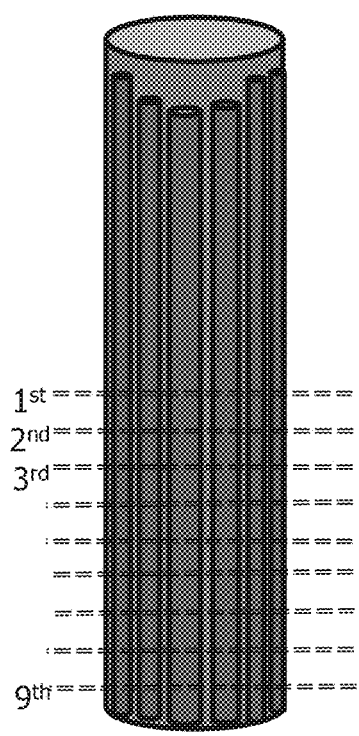
Figure 8B:
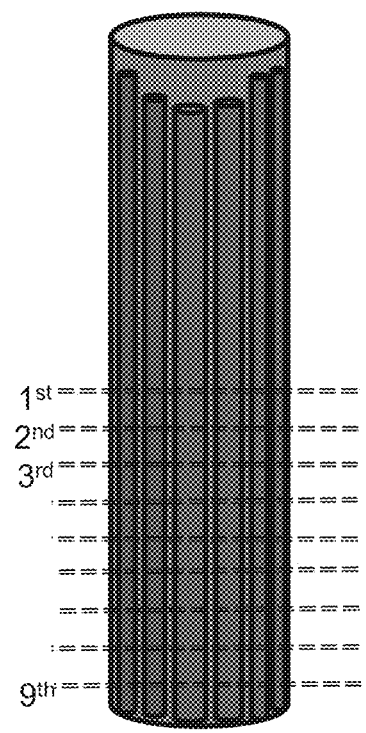

FIGS. 8A and 8B are schematic illustrations of a sub-millimeter phantom, uniquely designed to model different tissue compartmentations within a single imaged voxel. The phantom consists of 2 (FIG. 8A) and 3 (FIG. 8B) isolated compartments containing MnCl$_2$ solutions at different concentrations: (1) tubes with short $T_2$=15 ms modeling myelin water (small yellow tubes); (2) tubes with longer $T_2$=80 ms modeling the intra/extra water in the 3-compartment model (small magenta tubes); (3) background with $T_2$=65 ms and $T_2$=50 ms in the 2- and 3-compartment phantoms, respectively, modeling the intra/extra water (two large gray tubes). To model disease progression a series of consecutive phantom scans with varying internal compartmentations were performed, corresponding to an increase in the short $T_2$ fractions (e.g., myelin content). To acquire multi-voxel data each scan was repeated 10 times, each time with varying slice offset: {−0.4, −0.3, . . . , 0.3, 0.4} mm and 9 slices (indicated in dashed black lines). Additional high-resolution phantom scans (containing 64×64 voxels per slice) were performed.

FIGS. 9A-L show results of a repeatability test applied to the method of the present embodiments on in vivo brain data. Shown are parametric maps of white matter (WM) segments from 3 consecutive scans of the same subject using the method of the present embodiments. FIGS. 9A-C show mask and myelin water fraction (MWF) maps of genu of corpus callosum (GCC), FIGS. 9E-H show mask and MWF maps of splenium of corpus callosum (GCC), and FIGS. 9I-L show mask and MWF maps of a cortical WM segment. MWF maps are presented with the same color scale and on top of a $T_2$ map presented in gray scale.

Figure 10:
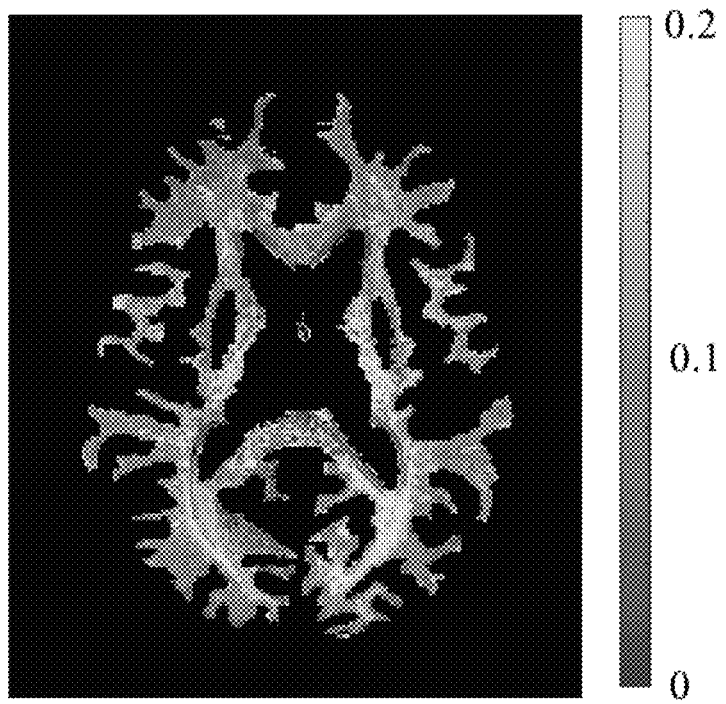

FIG. 10 shows myelin water map produced from in vivo brain data of a healthy subject, using a method of mapping transverse relaxation times according to some embodiments of the present invention.

Figure 11:
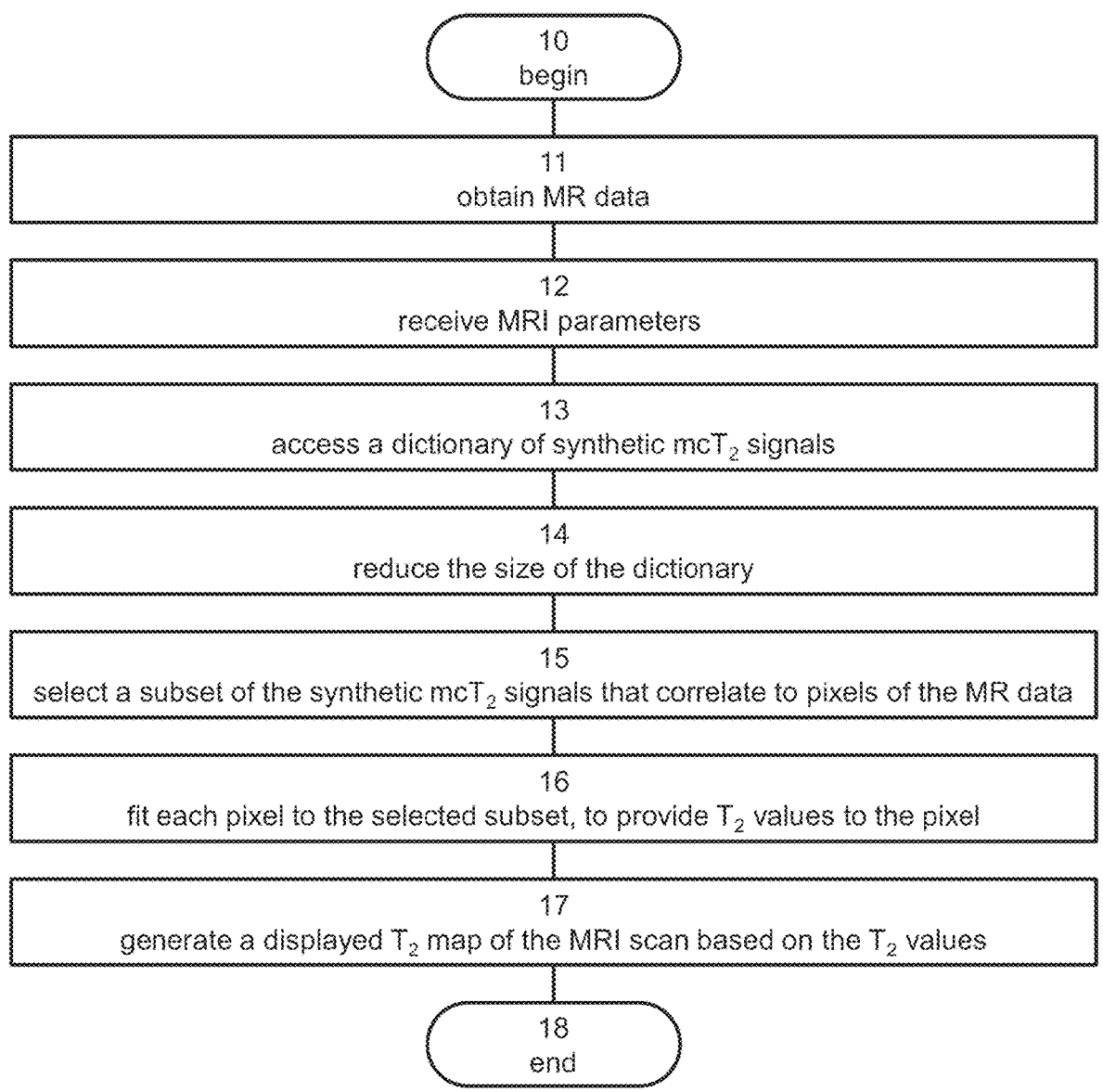

FIG. 11 is a flowchart diagram of a method suitable for mapping $T_2$ values in an MRI scan, according to some exemplary embodiments of the present invention.

Figure 12:
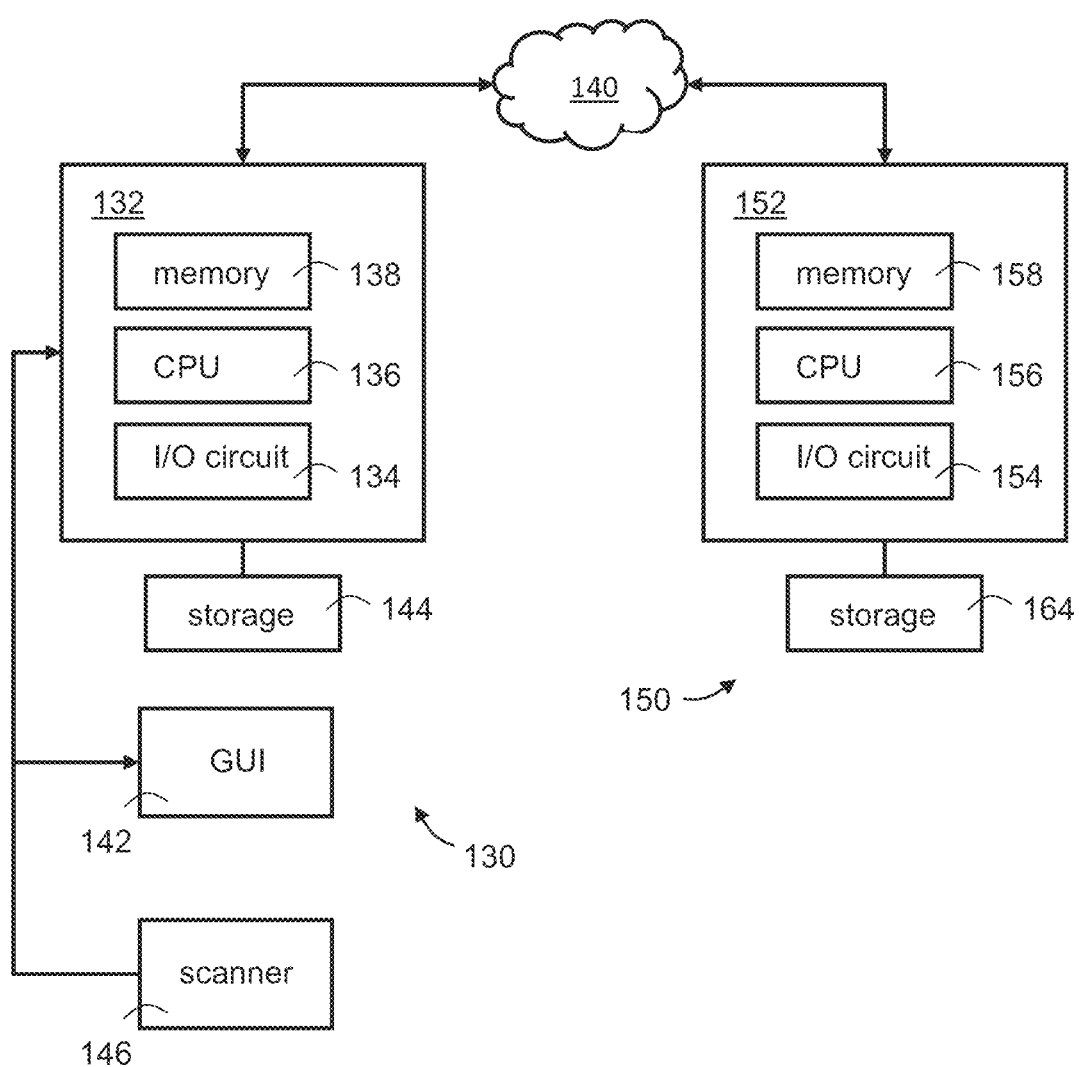

FIG. 12 is a schematic illustration of a computer system which can be used to execute the method described in FIG. 11.

DESCRIPTION OF SPECIFIC EMBODIMENTS
OF THE INVENTION

The present invention, in some embodiments thereof, relates to a magnetic resonance and, more particularly, but not exclusively, to a method and system for analyzing multi-component magnetic resonance signals.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 11 is a flowchart diagram of a method suitable for mapping $T_2$ values in an MRI scan, according to various exemplary embodiments of the present invention.

It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

At least part of the operations described herein can be implemented by a data processing system, e.g., a dedicated circuitry or a general purpose image processor, configured for receiving MR data and executing the operations described below. At least part of the operations can be implemented by a cloud-computing facility at a remote location.

Computer programs implementing the method of the present embodiments can commonly be distributed to users by a communication network or on a distribution medium such as, but not limited to, a floppy disk, a CD-ROM, a flash memory device and a portable hard drive. From the communication network or distribution medium, the computer programs can be copied to a hard disk or a similar intermediate storage medium. The computer programs can be run by loading the code instructions either from their distribution medium or their intermediate storage medium into the execution memory of the computer, configuring the computer to act in accordance with the method of this invention. During operation, the computer can store in a memory data structures or values obtained by intermediate calculations and pull these data structures or values for use in subsequent operation. All these operations are well-known to those skilled in the art of computer systems.

Processing operations described herein may be performed by means of processer circuit, such as a DSP, microcontroller, FPGA, ASIC, etc., or any other conventional and/or dedicated computing system.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

The method of the present embodiments is suitable for mapping $T_2$ values of a preclinical MRI scan, e.g., an MRI scan performed using an MR scanner having a relatively small bore size (e.g., less than 50 cm or less than 40 cm, e.g., 30 cm or less), or a clinical MRI scan, e.g., an MRI scan performed using a whole-body or a head MR scanners, such as, but not limited to, an MR whole-body scanner generating magnetic field of at least 7T or at least 10.5T scanners, or an MR head scanner generating magnetic field of at least 15T.

The method begins at 10 and optionally and preferably continues to 11 at which MR data are acquired from at least a portion of a body of a human or an animal subject, preferably a living human or an animal subject. The body portion can be, for example, the brain of the subject. Also contemplated are embodiments in which the body portion includes a skeletal muscle, a cartilage, and/or a breast. Further contemplated are embodiments in which the MR data are acquired from the whole body of the subject, or from multiple portions of the body of the subject.

The MR data describe an MR signal which can be acquired by an MR scanner having a controller configured for generating a pulse sequence suitable for acquiring an MR signal from which MR data can be obtained. Preferably, the pulse sequence is selected to allow extraction of relaxation time values from the generated MR data, particularly $T_2$ values. For example, the pulse sequence can be a $T_2$ weighted pulse sequence. In some embodiments of the present invention the pulse sequence is a multi-echo spin-echo (MESE) pulse sequence, oftentimes abbreviated in the literature as a multi spin-echo sequence, which typically includes an initial 90 degree pulse and a series of 180 degree pulses, each followed by an echo, thus providing a train of echo signals. Variants of the MESE pulse sequence and other types of pulse sequences are also contemplated according to some embodiments of the present invention. In various exemplary embodiments of the invention the MR data describe $mcT_2$ scan signals.

Alternatively, instead of acquiring the MR signal using an MR scanner, the MR data can be received from a local computer readable storage medium or from a remote data source over a communication network.

The MR data (either obtained from an MR scanner, or received from a local or remote source) is defined over a plurality of pixels, each being associated with a multicomponent $T_2$ ($mcT_2$) scan signal. In some embodiments of the present invention the method is executed without any a priori assumption regarding the number of components in the $mcT_2$ signal of each pixel.

Optionally, the method proceeds to 12 at which a set of MRI parameters is received. The MRI parameters are the parameters that were employed by the MR scanner in order to generate the MR data, and may include, for example, one or more of the following MRI parameters: matrix size, field-of-view (FOV), slice thickness, bandwidth (BW), pulse shape, refocusing angle, echo time (TE), repetition time (TR), a spatial distribution of the main magnetic field $B_0$, a frequency off-resonance of $B_0$, a spatial distribution of the secondary field $B_1$, and a radio-frequency (RF) pulse amplitude. The parameters can be obtained directly from the MR scanner or from a local storage medium or over a communication network.

The method proceeds to 13 at which a computer readable medium storing an $mcT_2$ dictionary having a set of synthetic $mcT_2$ signals is accessed. Each synthetic $mcT_2$ signal of the set preferably includes a function describing a time-dependence of an MR amplitude that corresponds to a transverse relaxation of water molecules that is characterized by a plurality of different $T_2$ values. The functions can be provided numerically, e.g., as lookup tables, or they can be provided in parameterized forms, e.g., as sums of exponential decay forms parameterized according to the respective $T_2$ values. The different $T_2$ values can include, for example, $T_2$ values corresponding to an intracellular water fraction, $T_2$ values corresponding to an extracellular water fraction, $T_2$ values corresponding to a myelin water fraction (MWF), $T_2$ values corresponding to a macromolecule-bound water fraction, and/or $T_2$ values corresponding to solid macromolecules.

In some embodiments of the present invention the computer readable medium stores more than one set of synthetic $mcT_2$ signals, where each set is associated with a different set of MRI parameters, e.g., of the types obtained at 12. In these embodiments, the method selects the set of synthetic $mcT_2$ signals based on the values of the parameters obtained at 12.

The $mcT_2$ dictionary is preferably a previously prepared $mcT_2$ dictionary. Alternatively, the $mcT_2$ dictionary can be constructed by the method and stored on the computer readable storage medium, prior to the execution of 13. The $mcT_2$ dictionary can be constructed based on the parameters obtained at 12. For example, the method can construct a single-component $T_2$ ($scT_2$) dictionary having a set of synthetic $scT_2$ signals, and then calculate each synthetic $mcT_2$ signal of the $mcT_2$ dictionary as a combination (e.g., a weighted sum) of a plurality of synthetic $scT_2$ signals. The $scT_2$ dictionary can be constructed by selecting a plurality of different predetermined $T_2$ values, and generating each synthetic $scT_2$ signal as a simulated echo modulation curve for one of the predetermined $T_2$ values. A representative example of a technique suitable for constructing an $mcT_2$ dictionary is described in the Examples section that follows.

In some embodiments of the present invention the method proceeds to 14 at which a range of $T_2$ values is identified for pixels in the MR data of the subject, and the size of the dictionary is reduced in response to this range. The range of $T_2$ values can be identified, for example, by applying two or more single-component $T_2$ ($scT_2$) analyses to the MR data. Each such $scT_2$ analysis provides one $T_2$ value, and the range of $T_2$ value can be identified based on these analyses. For example, the lowest and highest $T_2$ values obtained from the $scT_2$ analysis can delineate the range by bounding it from below and from above. The size of the dictionary can be reduced by dilution, wherein contribution to functions due to $T_2$ values that are outside the range are excluded from further consideration.

The method optionally and preferably proceeds to 15 at which a subset of the synthetic $mcT_2$ signals is selected from the dictionary. In some embodiments the selection 15 is executed based on a denoised version of the MRI scan, in which case operation 15 is preceded by a denoising operation applied to the MR data. The subset preferably includes those synthetic $mcT_2$ signals for which the correlations between the synthetic $mcT_2$ signals and pixels in the MR data (or pixels in the denoised MR data) are the highest among the set. The present embodiments contemplate any type of calculation that provides a correlation. Representative examples of such calculations including, without limitation, distance based norms, e.g., $L_p$-norms, particularly $L_2$-norms.

It is appreciated that since each pixel is associated with a $mcT_2$ signals, the correlations may differ among different pixels. Thus, according to some embodiments of the present invention the method sums correlations across multiple pixels for each synthetic $mcT_2$ signal, and uses this summation to select the synthetic $mcT_2$ signals.

In some embodiments of the present invention a non-linear transformation is applied to the correlation values, before the summation, so as to prioritize synthetic $mcT_2$ signals which present high correlation with a low number of pixels. One, non-limiting example of such non-linear transformation is to raise all the correlations to the power of $1 \leq \beta \leq 10,000$. This operation is beneficial in detection focal pathology points within the analyzed segment.

The method proceeds to 16 at which for each of at least a portion of the pixels of the MR data (e.g., each pixel in a region-of-interest with the MRI scan), the respective $mcT_2$ scan signal is fitted to the selected subset to provide a plurality of $T_2$ values for each pixel. Preferably, the fit 16 is executed based on the selected subset and without any a priori assumption regarding the number of different $T_2$ values for the pixel. In other words, the number of different $T_2$ values obtained for a particular pixel are based on the fitting operation between the pixel data and the synthetic signals selected according to the correlation with the data, without executing any preselection of the number of $T_2$ values ahead of the fit. This is advantageous over traditional techniques which define a priori the number of $T_2$ values in the pixel, and only then perform the fitting based on the defined number of $T_2$ values.

The method proceeds to 17 at which a $T_2$ map of the MRI scan is generated based on the $T_2$ values obtained at 16 and displayed, for example, on a display device, and/or transmitted to a computer readable storage medium, or over a communication network.

The method ends at 18.

FIG. 12 is a schematic illustration of a client computer 130 having a hardware processor 132, which typically comprises an input/output (I/O) circuit 134, a hardware central processing unit (CPU) 136 (e.g., a hardware microprocessor), and a hardware memory 138 which typically includes both volatile memory and non-volatile memory. CPU 136 is in communication with I/O circuit 134 and memory 138. Client computer 130 preferably comprises a graphical user interface (GUI) 142 in communication with processor 132. I/O circuit 134 preferably communicates information in appropriately structured form to and from GUI 142. Also shown is a server computer 150 which can similarly include a hardware processor 152, an I/O circuit 154, a hardware CPU 156, a hardware memory 158. I/O circuits 134 and 154 of client 130 and server 150 computers can operate as transceivers that communicate information with each other via a wired or wireless communication. For example, client 130 and server 150 computers can communicate via a network 140, such as a local area network (LAN), a wide area network (WAN) or the Internet. Server computer 150 can be in some embodiments be a part of a cloud computing resource of a cloud computing facility in communication with client computer 130 over the network 140.

GUI 142 and processor 132 can be integrated together within the same housing or they can be separate units communicating with each other. GUI 142 can optionally and preferably be part of a system including a dedicated CPU and I/O circuits (not shown) to allow GUI 142 to communicate with processor 132. Processor 132 issues to GUI 142 graphical and textual output generated by CPU 136. Processor 132 also receives from GUI 142 signals pertaining to control commands generated by GUI 142 in response to user input. GUI 142 can be of any type known in the art, such as, but not limited to, a keyboard and a display, a touch screen, and the like.

Client 130 and server 150 computers can further comprise one or more computer-readable storage media 144, 164, respectively. Media 144 and 164 are preferably non-transitory storage media storing computer code instructions for executing the method as further detailed herein, and processors 132 and 152 execute these code instructions. The code instructions can be run by loading the respective code instructions into the respective execution memories 138 and 158 of the respective processors 132 and 152.

In some embodiments of the present invention, MR data describing an MR signal is transmitted to processor 132 by means of I/O circuit 134. I/O circuit 134 can receive the MR data via GUI 142, read it from storage medium 144, or receive it from an MR scanner 146. Processor 132 receives the MR data, and can transmit it to server computer 150, which can execute the method as described herein and transmit the $T_2$ map back to computer 130 over network 140. Computer 130 can receive the $T_2$ map from computer 150 and display it on GUI 142 or stores them in storage medium 144. Alternatively, processor 132 can execute the method as described herein, in which case it is not necessary to transmit the MR data to computer 150.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

The MRI signal is sensitive to microscopic processes occurring at a scale smaller than image resolution but is limited in visualizing them due to a hard limit on achievable resolutions (approximately 1 mm³ voxels). Therefore, probing microstructural features is done indirectly by deconvolving the MRI signal into its different components and their relative amounts. This multicomponent analysis is usually applied to biological tissues with microstructural order where a small number of specific water pools (tissue compartments) can be identified. An example of such ordered tissue is the brain white matter, where 3 distinct water environments exist: intracellular water, extracellular water, and water that reside between myelin sheaths. Estimating the relative myelin water fraction is of the high interest as it reflects the local myelin content, which is a valuable biomarker for myelodegenerative disorders and neuronal developmental processes.

Multicomponent analysis can be done via quantification of the $T_2$ relaxation time. To that end, a designated signal processing algorithm, known as multicomponent $T_2$ analysis (mc$T_2$), translates the $T_2$ signal into a $T_2$ distribution describing the different microscopic tissue compartments. The relative portion of the short peak in the obtained $T_2$ distributions is considered as myelin water fraction.

This Example describes a signal processing approach for mc$T_2$ analysis, which includes studying spatially global features of the tissue using statistical tools. After identifying a tissue-specific set of possible $T_2$ spectra, the method of the present embodiments uses these to locally analyze each voxel, while still imposing local smoothness constraints. The statistical power produced by this data-driven approach endows the whole process with additional robustness, which in turn stabilizes the analysis. Unlike conventional approaches, the method described herein does not impose a priori assumptions about the number of compartments within the pixel, but rather learns the compartmentation regime from the data. While other techniques rely on the exponential decay pattern the method according to some embodiments of the present invention is based on a signal model which produces accurate and reproducible $T_2$ signals across different scanners and scan setting. The method of the present embodiments can be easily integrated, as a post processing module, to any clinical MRI scanner for visualizing microscopic processes in vivo (physiological and pathological).

The method described herein optionally and preferably assumes the acquired signal is a weighted combination of an unknown number of microscopic substrates with distinct $T_2$ values and that the pixels of the MRI scan have mutual compartmentation features.

Using statistical power of global correlations between voxels within the tissue segment the method optionally and preferably selects an optimal set of basis compartmentations for the fitting task. The Inventors found that this dramatically reduces ambiguity in solution space.

In some embodiments of the present invention the optimal set is selected from a large set of simulated MRI signals spanning the entire range of possible microscopic substrates combinations. The simulated signals are created by a signal model that takes into account specific protocol implementation, hardware imperfections, and scan parameters to composite inherent artifacts present at every MRI scan.

The method of the present embodiments optionally and preferably provides a set of sub-voxel $T_2$ values that corresponds to physiological parameters such as, but not limited to, the relative fraction of each compartment, and its biochemical state.

An advantage of the method of the present embodiments is that it can learn the anatomy in a global manner, prior to analyzing each specific voxel. An additional advantage of the method of the present embodiments is that it does not impose prior distribution of $T_2$ spectrum. A further advantage of the method of the present embodiments is that it does not use a predefined fixed number of components, but rather manages to accurately identify this number based on the acquired data.

The method of the present embodiments can be applied to MRI scans of biological tissues to visualize physiological and pathological process that occur at the microscopic level in vivo. The method of the present embodiments can thus be used to probe early disease biomarkers and developmental processes.

EXPERIMENTAL

Multicomponent $T_2$ analysis can be highly valuable for probing tissue microstructure. For example, myelin water fraction (MWF), which is a proxy for myelin content, can be estimated using mc$T_2$ analysis. This estimation is conventionally done through a fitting process where a weighted sum of different $T_2$ components is matched to multi-echo spin-echo (MESE) signal decay curve. However, the detection of the true $T_2$ distribution is a highly ill-posed problem, especially at low-to-moderate signal-to-noise ratios (SNRs), which characterize most MRI data.

The method of the present embodiments tackles the high-dimensionality of this problem, using correlations between local and global features of the anatomy in question. The accuracy of the method of the present embodiments is demonstrated below on phantoms and in vivo. The results demonstrate that the method of the present embodiments can accurately identify microscopic compartments, operate at realistic scan times, and be used estimate to estimate myelin content in vivo.

The following description concerns mc$T_2$ analysis from MESE signals. To overcome the problem's non-uniqueness the method of the present embodiments generates a dictionary of possible $T_2$ distributions of different tissue types, and exploit correlation between local and global features to choose a small set of basis-functions for the fitting process. The method can be applied to clinical MESE data and the resultant spectra can be further analyzed to identify different tissue microenvironments, as well as, to quantify MWF.

Methods mc$T_2$ Dictionary

FIG. 6 is a flowchart showing a method suitable for constructing a data driven mc-$T_2$ signals dictionary, according to some embodiments of the present invention. (A) multi-component $T_2$ signals (mc$T_2$) are acquired and scan protocol parameters are given to a signal-model (echo-modulation-curve method), to optionally and preferably produce a dictionary of simulated single-$T_2$ signals. (B) The dictionary is used as the basis for an expanded dictionary containing a set of mc$T_2$ signals. This expansion is optionally and preferably obtained by averaging M single-$T_2$ decay curves (M=1,2 or 3 in the present Example) with varying weighting that span the physiological range of possible microstructural tissue configurations. (C) Experimental mc$T_2$ signals are optionally and preferably denoised, for example, using a PCA-based denoising scheme. (D-E) Data of selected brain region are utilized for a $T_2$ map to identify the range of single $T_2$ values in the segment. (F) The detected range of the single-$T_2$ values is used to filter out mc$T_2$ that do not average to a $T_2$ value that matches to $T_2$ values within the segment.

FIG. 7 is a flowchart showing a method suitable for selecting a segment-specific set of mc$T_2$ basis elements, according to some embodiments of the present invention. A correlation-based score is computed between the (denoised) signal from each voxel in the brain segment vis-à-vis the set of dictionary elements. Scores are normalized and a nonlinear metric is applied to the scores in order to prioritize the multi-$T_2$ signals according to their probability to be found within the segment. To that end, each score is raised by a power of a predetermined parameter denoted by β, which is optionally and preferably larger than 1. The advantage of using the power parameter is that it prioritizes $mcT_2$ signals with higher scores, yet for a relatively small number of voxels in the segment, in comparison to signals that match much larger number of voxels but with smaller score. Such high scores can arise, for example, for a small lesion within a large anatomical segment. By raising the normalized score to the power of β>1 the method of the present embodiments mathematically prioritizes signals with very high scores, even when those signals match the data for a small number of voxels.

Fitting

A single $T_2$ is fitted to each MESE signal. To compensate for the non-exponential signal decay due to stimulated and indirect echoes the echo modulation curve (EMC) method is employed. This technique was previously shown to produce accurate and reproducible $T_2$ values, by accounting for specific protocol implementation, hardware imperfections, and scan parameters to form a simulated MESE signal. The same model is used to simulate a series of multi-$T_2$ signals each containing from 1 to 3 components, with relative fractions, which in this Example are selected between 0.1 and 1:

$$S_{mc} = \sum_{i=1}^{3} \omega_i \cdot S_{T_2^i} \text{ s.t. } \sum_{i=1}^{3} \omega_i = 1$$

where $S_{T2}$ is the MESE relaxation pattern for the $i^{th}$ $T_2$, $w_i$ is the relative fraction of the $T_2$ component, and $S_{mc}$ is the simulated multicomponent-MESE signal.

For each simulated signal a score is calculated optionally and preferably based on its $L_2$-norm correlation to each of the pixels in the segment of interest. These scores are preferably summed up, producing a global similarity score for each simulated multi-$T_2$. Multi-$T_2$ signals with the highest scores among the set are defined as the basis functions. In this Example, 50 basis functions were selected. The basis functions were used for the optimization process of the MRI scan. The problem was defined as a quadratic least-squares and a quadratic programming solver with $L_1$ regularization term was applied on the set for the fitting task.

Validation

Numeric Simulation

A 2D Shepp-Logan numerical phantom was generated, consisting of 5 tissue types (FIGS. 1A-B). Each type reflected a different distribution of three T components (detailed in FIGS. 1A-B) with varying fractions (detailed in FIGS. 2A-E). The MESE signal from each compartment was simulated using a weighted-sum of the components at each pixel in the phantom. To simulate realistic scan conditions, Gaussian noise, and natural variation of 20% in $T_2$ values were added to the signals prior to analysis.

Phantom Scans

A unique multi-compartment $T_2$ phantom was prepared from 3 $MnCl_2$ solutions inducing different $T_2$ values (FIGS. 8A and 8B). A 50 ms solution was filled within a 5 mm tube with a varying number of 1 mm tubes filled with $T_2$={13 and 80 ms}. Smaller tubes were consecutively inserted between scans into the 5 mm tube. The phantom was scanned 7 times on a Bruker, 9.4T scanner with a different number of small tubes inducing varying fractions. This phantom's design allowed the Inventors of the present invention to map high-resolution $T_2$ values in all three environments and to perform a low-resolution scan where all three compartments occupied a single pixel. Low resolution data was deconvolved using the method of the present embodiments and the resulting $T_2$ spectra were validated against ground-truth values. To estimate MWF, the areas under the short $T_2$ components were calculated from the resultant $T_2$ spectra.

In Vivo

MESE brain data (30 echoes and 2 averages) were acquired from healthy mouse (Bruker, 7T) and human volunteer (Siemens, 3T). $T_2$ spectra were fitted to all voxels and MWF were estimated in selected WM pixels.

Results $T_2$ spectra of numerical phantom were perfectly reconstructed with 1, 2 and 3 compartments respectively, and at SNR level of 60 and above (FIGS. 2A-E).

Figure 2A:
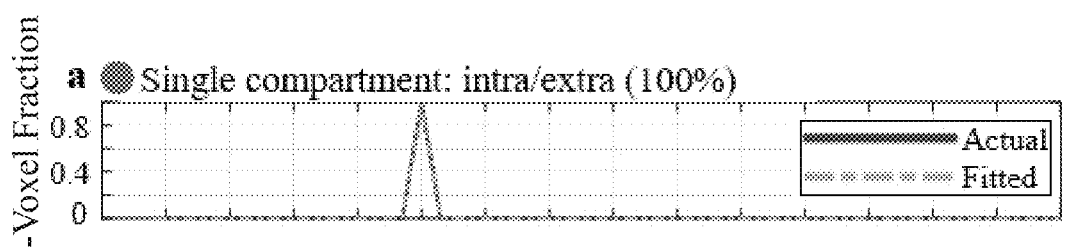
Figure 2B:
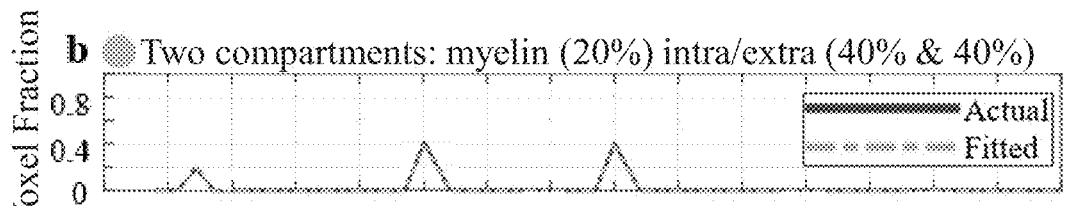
Figure 2C:
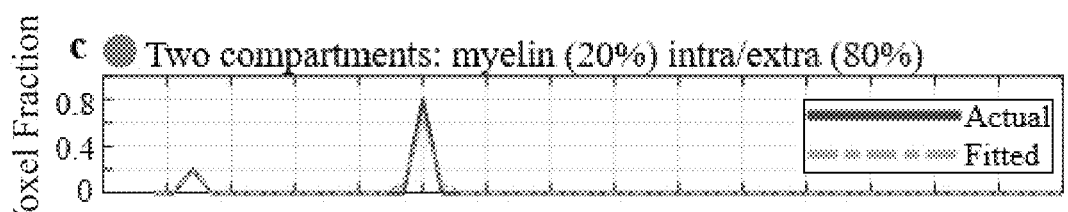
Figure 2D:
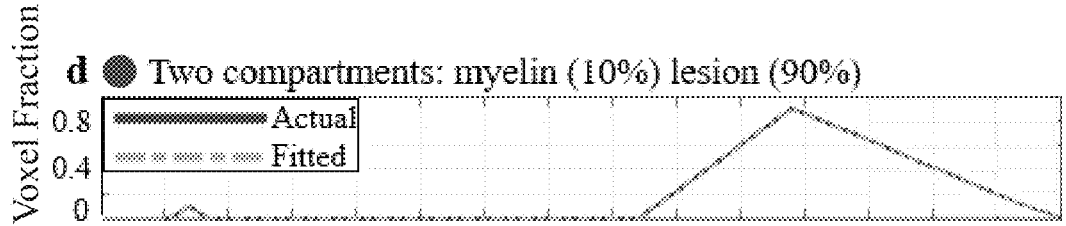
Figure 2E:
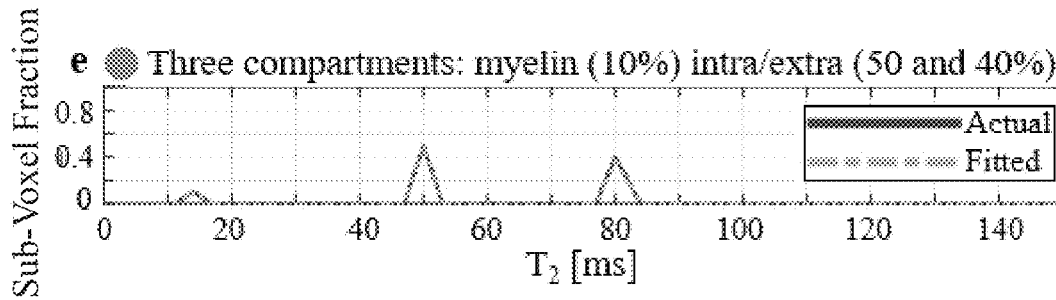
Figures 3A, 3B:
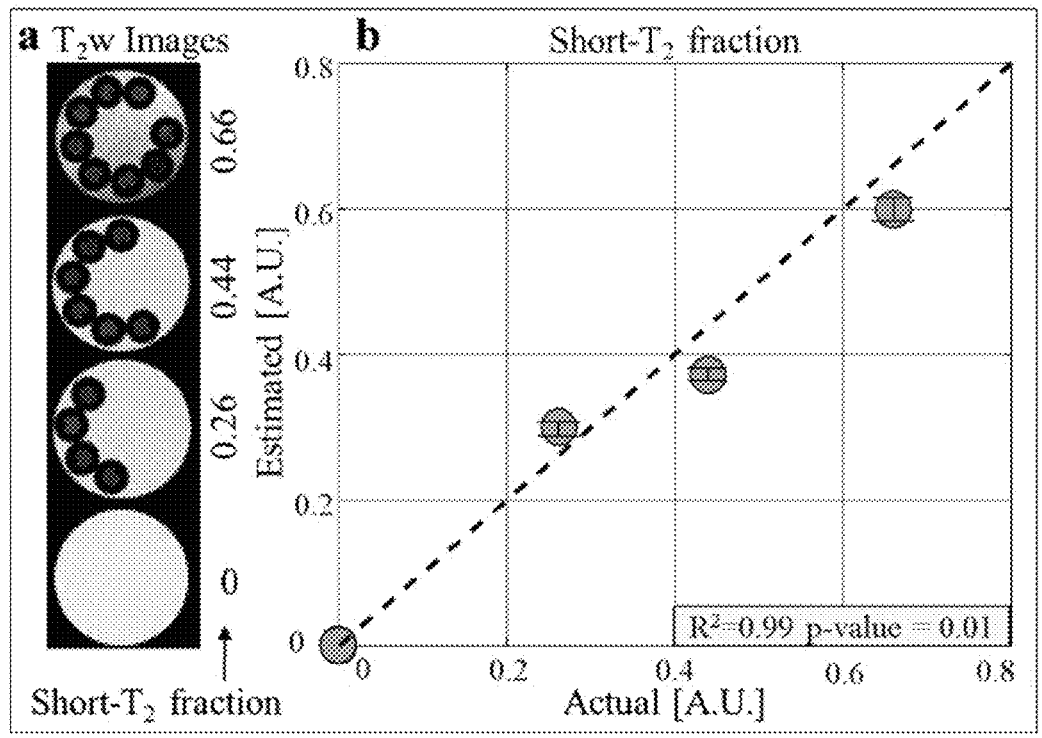
Figures 3C, 3D:
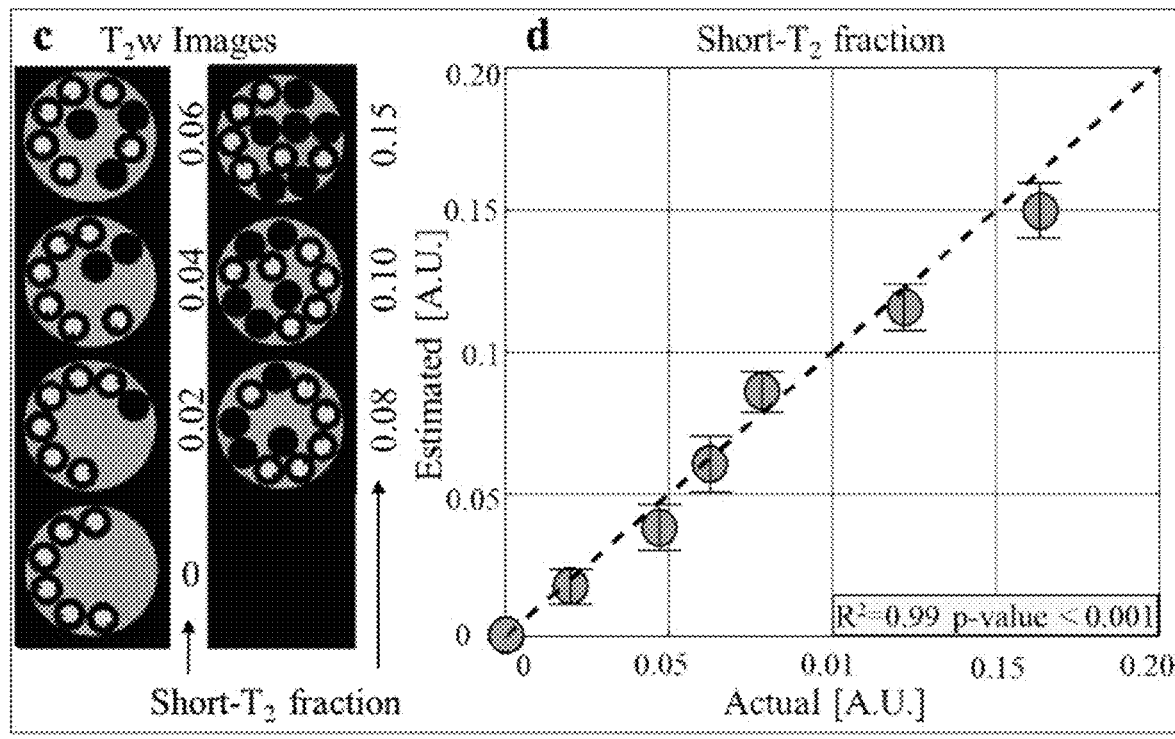

FIGS. 3A-D show validation of the $mcT_2$ fitting algorithm on a physiological sub-millimeter two- and three-compartment phantom. FIGS. 3A and 3C shows four (FIG. 3A) and seven (FIG. 3D) consecutive MRI high-resolution scans of two- and three-compartment compartment sub-voxel phantoms, with increasing fraction of the short-$T_2$ component resembling the myelin water fraction (MWF). The phantom in FIG. 3A contained two $T_2$ compartments: 11 ms to model myelin water (dark-gray circles) and 60 ms to model both intra-/extra-axonal water pools (light-gray background), respectively. The phantom in FIG. 3C phantom contained 3 compartments: 11 ms, 51 ms and 80 ms to model myelin water (black circles), and intra-/extra-axonal water pools (dark-gray background and light-gray circles). These values were selected to model myelinated brain tissue content. The short-$T_2$ fraction was defined as the division of the area under the short $T_2$ component by the area of the entire distribution, and was estimated to model MWF. FIGS. 3B and 3D show agreements between the actual and the reconstructed short-$T_2$ fractions ($r^2$ values of 0.98, and 0.98, and p-values of 0.91, and less than 0.01 for the two- and three-compartment phantoms, respectively). A 45° line representing perfect agreement is shown as a dashed line.

FIG. 10 shows myelin water map, produced from in vivo brain data of a healthy subject using the technique of the present embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

[1] Heath F, Hurley A, et al. Advances in noninvasive myelin imaging. Dev. Neurobiol. 2018; 78:136-151.
[2] Zhang, J, Kolind S, et al. Comparison of Myelin Water Fraction Brain Images Using Multi-Echo $T_2$-Weighted GRASE Relaxation and Steady-State Methods. Proc Intl Soc Mag Reson Med. 2015; 73(1):1025-1029.
[3] McCreary R, et al. Multiexponential T2 and magnetization transfer MRI of demyelination and remyelination in murine spinal cord. Neuroimage. 2009; 45(4):1173-1182.
[4] Möller E, et al. Iron, Myelin, and the Brain: Neuroimaging Meets Neurobiology. Trends Neurosci. 2019; 42(6): 384-401.
[5] Alonso-Ortiz E, Levesque R, et al. MRI-based myelin water imaging: A technical review. Magn. Reson. Med. 2015; 73(1):70-81.
[6] Whittall P and MacKay L. Quantitative interpretation of NMR relaxation data. J. Magn. Reson. 1989; 84:134-152.
[7] Laule C, et al. Water content and myelin water fraction in multiple sclerosis—a T2 relaxation study. J. Neurol. 2004; 251:284-293.
[8] Whittall P, et al. In vivo measurement of $T_2$ distributions and water contents in normal human brain. Magn. Reson. Med. 1997; 37:34-43.
[9] Bouhrara M, Spencer G. Improved determination of the myelin water fraction in human brain using magnetic resonance imaging through Bayesian analysis of mcDESPOT. Neuroimage. 2019; 127:456-471.
[10] Hennig J. Multiecho imaging sequences with low refocusing flip angles. J Magn Reson 1988; 78:397-407.
[11] Ben-eliezer N, Sodickson D K, et al. Rapid and Accurate T2 Mapping from Multi-Spin-Echo Data Using Bloch-Simulation-Based Reconstruction. 2015; 73(2): 809-817.
[12] MacKay L, Laule C. Magnetic Resonance of Myelin Water: An in vivo Marker for Myelin. Brain Plast. 2016; 2:71-91.
[13] Kathryn W, Nathaniel K, et al. Myelin water fraction imaging with MRI. NeuroImage 2018; 2:511-521.

What is claimed is:

1. A method of mapping transverse relaxation times ($T_2$) in a magnetic resonance imaging (MRI) scan defined over a plurality of pixels, each being associated with a multicomponent $T_2$ (mc$T_2$) scan signal, the method comprising:
   accessing a computer readable medium storing an mc$T_2$ dictionary having a set of synthetic mc$T_2$ signals;
   selecting a subset of synthetic mc$T_2$ signals for which correlations between said synthetic mc$T_2$ signals and pixels in the MRI scan are highest among said set;
   for each of at least a portion of said pixels, fitting a respective mc$T_2$ scan signal to said subset to provide, a plurality of T2 values for said pixel; and
   generating a displayed $T_2$ map of said MRI scan based on said T2 values.

2. The method according to claim 1, wherein said selecting comprises calculating $L_2$-norms thereby obtaining said correlations.

3. The method according to claim 1, comprising summing correlations across multiple pixels for each synthetic mc$T_2$ signal, wherein said selection is based on said summations.

4. The method according to claim 1, comprising constructing said mc$T_2$ dictionary from mc$T_2$ data of said MRI scan.

5. The method according to claim 4, comprising receiving magnetic resonance (MR) scan protocol parameters associated with said mc$T_2$ scan signals, wherein said constructing said is based on said scan protocol parameters.

6. The method according to claim 4, comprising constructing a single-component $T_2$ (sc$T_2$) dictionary having a set of synthetic sc$T_2$ signals, wherein said constructing said mc$T_2$ dictionary comprises calculating each synthetic mc$T_2$ signal as a combination of a plurality of synthetic sc$T_2$ signals.

7. The method according to claim 6, wherein said constructing said sc$T_2$ comprises selecting a plurality of different predetermined $T_2$ values, and generating each synthetic sc$T_2$ signal as a simulated echo modulation curve for one of said predetermined $T_2$ values.

8. The method according to claim 1, comprising, prior to said selection, identifying a range of $T_2$ values for said at least said portion of said pixels, and diluting said mc$T_2$ dictionary based on said identified range.

9. The method according to claim 1, comprising denoising said MRI scan, prior to said selection.

10. The method according to claim 1, wherein said MRI scan is a multiple echo spin-echo MRI scan.

11. The method according to claim 1, wherein said MRI scan is a preclinical MRI scan.

12. The method according to claim 1, wherein said MRI scan is a clinical MRI scan.

13. The method according to claim 1, wherein at least one of said plurality of $T_2$ values corresponds to a water fraction selected from the group consisting of intracellular water fraction, and extracellular water fraction.

14. The method according to claim 1, wherein said MRI scan comprises an MRI scan of a brain.

15. The method according to claim 1, wherein said MRI scan comprises an MRI scan of at least one of a skeletal muscle, a cartilage, and a breast.

16. The method according to claim 1, wherein at least one of said plurality of $T_2$ values corresponds to a myelin water fraction (MWF).

17. The method according to claim 1, wherein at least one of said plurality of $T_2$ values corresponds to a macromolecule-bound water fraction.

18. The method according to claim 1, wherein at least one of said plurality of $T_2$ values corresponds to a solid macromolecule.

19. The method according to claim 1, being executed without any a priori selection of a number of different $T_2$ values for the pixel.

20. A non-transitory computer software product, comprising a computer-readable medium in which program instructions are stored, which instructions, when read by a data processor, cause the data processor to receive at least a magnetic resonance imaging (MRI) scan, and to execute the method according to claim 1.

* * * * *